United States Patent [19]
Snyder

[11] 4,040,299
[45] Aug. 9, 1977

[54] AIR SAMPLING APPARATUS
[75] Inventor: Louis J. Snyder, Baton Rouge, La.
[73] Assignee: Ethyl Corporation, Richmond, Va.
[21] Appl. No.: 523,342
[22] Filed: Nov. 13, 1974
[51] Int. Cl.² .............................................. G01N 1/24
[52] U.S. Cl. .............................. 73/421.5 R; 23/232 R; 23/254 R; 23/259
[58] Field of Search ................ 23/259, 292, 232 R, 23/254 R; 73/421.5 R, 422 R, 24

[56] References Cited
U.S. PATENT DOCUMENTS

| | | |
|---|---|---|
| 2,569,895 | 10/1951 | Main-Smith et al. ............ 23/232 R X |
| 3,618,393 | 11/1971 | Principe et al. ................. 73/421.5 R |
| 3,635,092 | 1/1972 | Maughan et al. ................. 23/259 X |
| 3,699,814 | 10/1972 | Kaufman ......................... 73/421.5 R |
| 3,817,100 | 6/1974 | Anderson et al. ............ 73/421.5 R X |
| 3,866,474 | 2/1975 | Hasselmann ................... 73/421.5 R |
| 3,884,081 | 5/1975 | Griffith ......................... 73/421.5 R |
| 3,950,136 | 4/1976 | Bellinga ....................... 73/421.5 R X |

Primary Examiner—Norman Yudkoff
Assistant Examiner—Barry I. Hollander
Attorney, Agent, or Firm—Donald L. Johnson; John F. Sieberth; James M. Pelton

[57] ABSTRACT

An apparatus for the continuous collection of a time-weighted gas sample is disclosed. The apparatus inclues a gas reservoir and an openable and closeable gas flow assembly communicating with the reservoir which assembly allows gas to flow at a constant rate from the exterior of the reservoir to the interior of the reservoir when there is a sufficient gas pressure differential between the exterior and interior of the reservoir so that the passing gas achieves a linear velocity in the throat of the gas flow assembly equal to the velocity of sound in the passing gas in the throat. The apparatus of this invention may also include additional gas sample removal assemblies attached to the reservoir.

6 Claims, 3 Drawing Figures

AIR SAMPLING APPARATUS

BACKGROUND OF THE INVENTION

For the protection of worker health, many industries have utilized air sampling apparatuses to determine the presence of harmful gaseous compounds which the worker may breathe. The determination of the quality of air in the work area breathed by the worker is oftentimes determined by having the worker carry with him, through a typical working day, an apparatus which is capable of sampling the air at a constant rate over a specified period.

Personal air sampling apparatuses worn generally include an electric pump and metering device which pumps a known volume of air into a gas collection reservoir over a known period of time. A metering device is used to help maintain a constant pump rate. Driving these pumps are batteries which require battery rechargers to recharge the battery after it has been used during a sampling period. Also, since the electric pump type apparatuses are not able to hold all of the air pumped during the day, these type apparatuses utilize an adsorbing section, to absorb from the air particular compounds which are being monitored. After the sampling period the adsorbent is removed from the apparatus and measurement is made of the various components adsorbed. In some instances the adsorbent is regenerative but in other cases it must be thrown away. A drawback in utilizing adsorbents is that the adsorbent utilized must be particularly chosen for the particular component that is sought to be identified in the air. Should there be a component in the air which has not been anticipated, or one which is not adsorbed by the particular adsorbent utilized, this particular component—even though harmful to the worker—may go undetected. Also, the component must be desorbed from the absorbent for analysis, thus leading to analytical errors.

Therefore it is seen that present day apparatuses, while useful, have drawbacks in that they require expensive electrical pumps, batteries and battery rechargers and also they have very poor broad spectrum capabilities.

Thus it is an object of this invention to provide an air collection apparatus which automatically collects an accurate time-weighted air sample which is not dependent upon energized collection means, operator attention, and which is capable of broad spectrum collection.

THE INVENTION

This invention relates to an apparatus for the continuous collection of gas for subsequent analysis which comprises: an enclosed gas reservoir, an openable and closeable gas flow assembly communicating with the gas reservoir for allowing gas to flow at a controlled rate from the exterior of the reservoir to the interior of the reservoir when there exists a sufficient gas pressure differential between the exterior and interior of the reservoir so that the passing gas achieves a linear velocity in the throat of the gas flow assembly equal to the velocity of sound in the passing gas in the throat. This invention may also include a separate gas sample removal evacuation assembly.

The gas flow assembly is preferably a capillary tube or a micrometer valve. However, it is to be understood that other orifices, nozzles, etc., which are capable of causing the passing gas to achieve a linear velocity in the throat of the orifice, nozzle, etc. which is equal to the velocity of sound of that gas in the throat are likewise applicable to the apparatus of this invention.

These and other features of this invention contributing satisfaction in use and economy in manufacture will be more fully understood from the following description of a preferred embodiment of this invention when taken in connection with the accompanying drawings wherein identical numerals refer to identical parts and in which.

Figure 1:
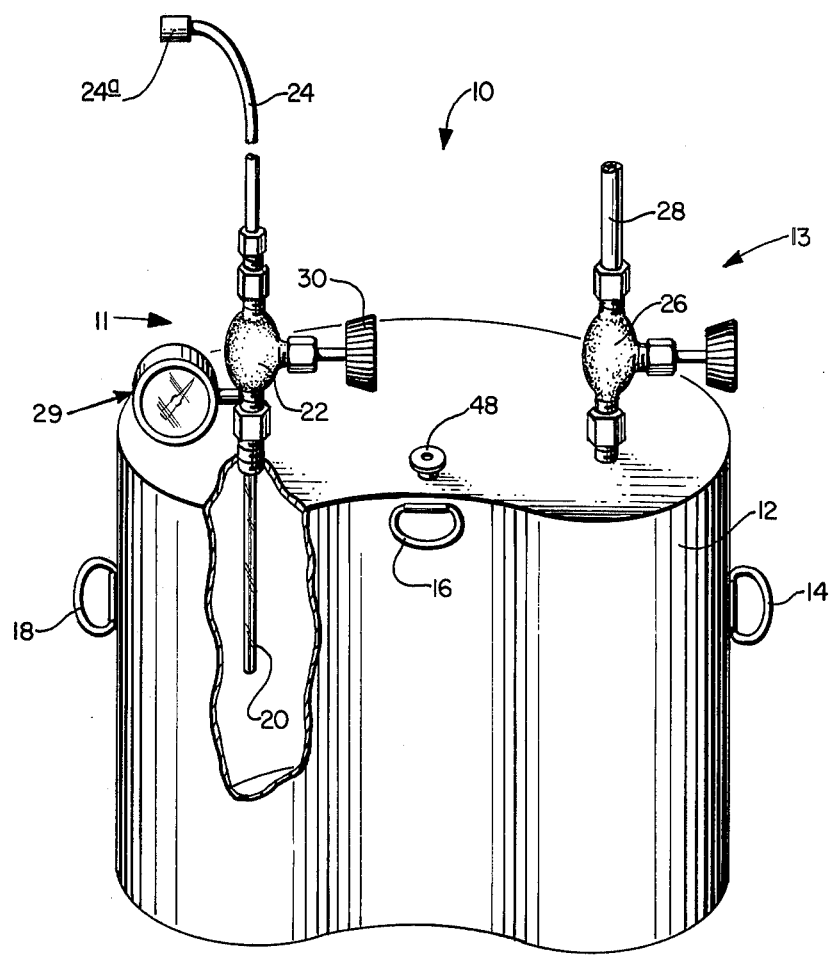
FIG. 1 is a perspective view, partially broken away, of an embodiment of this invention.

Referring now to FIG. 1, it can be seen that an apparatus of this invention, generally designated by the numeral 10, has an openable and closeable gas flow assembly, generally designated by the numeral 11, and two different optional gas sample removal assemblies, one being generally designated by the numeral 13 and the other by the numeral 48. Either one or both of these assemblies may be used at any one time.

As can be seen from the drawing, openable and closeable gas flow assembly 11 comprises a capillary tube 20 which penetrates a wall of gas reservoir 12 and is connected to one side of a valve 22, a gas admittance tube 24 connected on the other side of valve 22 and a filter 24a attached to gas admittance tube 24. Gas admittance tube 24 can be of any suitable non-reactive, non-adsorptive material such as nylon or teflon tubing and preferably extends to the vicinity of the wearer's breathing zone. Gas admittance tube 24 can have any suitable diameter, with diameters of from about 1/32 to about ¼-inch being preferred diameters. Openable and closeable valve 22 is a simple hand-controlled valve. Filter 24a is utilized to filter out any particulate matter which may be in the temperature and which would result in plugging of capillary 20. Particulate filters of non-adsorptive material such as fiberglass are suitable.

Connected to the other end of openable and closeable valve 22 is capillary 20. Capillary 20 may be made of glass or any other suitable material such as stainless steel, copper, etc.

Figure 2:
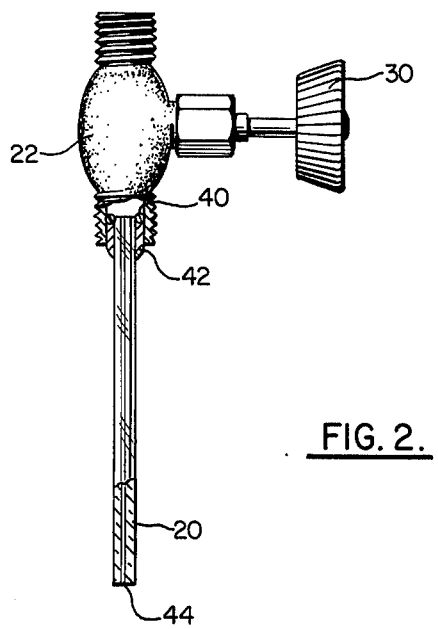
FIG. 2 is a detailed side elevational view, partially broken away, of the openable and closeable gas flow assembly shown in FIG. 1.

As can be seen in FIG. 2, attachment of capillary 20 to valve 22 is achievable by sealing capillary 20 with an epoxy seal 42 to openable and closeable valve 22. An O-ring 40 may also be utilized to insure as tight a seal as is possible. The inside diameter of the capillary tube can be of any convenient size, the capillary diameter size determining along with the reservoir volume, the length of time for which the gas will flow at the required linear velocity for a given starting pressure differential. A large diameter results in a shorter period of time for flow than a smaller diameter. Generally speaking, when the apparatus of this invention is utilized to sample air, a capillary having an inside diameter from about 0.01 mm to about 0.20 mm is suitable for use for collecting a sample over a period of up to about 24 hours in a reservoir having a volume of from about 250 cc to about 2000 cc and with a starting pressure differential of from about 30 inches of mercury to about 5 inches of mercury. A highly preferred apparatus is one which has a reservoir volume of about 700 cc and a capillary inside diameter of about 0.05 mm for a starting pressure differential of about 30 inches of mercury. It is also noted that devices other than capillary 20 may be utilized to achieve the aforementioned gas linear velocity which results in the favorable attributes of the apparatus of this invention. For example, a micrometer valve, which is adjustable to achieve the required gas linear velocities over the time desired, may be utilized. Other suitable substitutes are various nozzles and round-edge orifices. When using a micrometer valve for collecting an air sample over a period of four to eight hours in a reservoir having a volume of about 250 cc to about 2000 cc, valves which are adjustable to allow from about 0.5 to about 5.0 cc air/min. are preferred.

Although optional gas removing assemblies 13 and 48 are shown together on reservoir 12, they are not necessary for the obtainment of a gas sample from reservoir 12 as, in fact, gas flow assembly 11 may be operated in reverse to obtain the sample from the interior of reservoir 12. However, it has been found to be more convenient to utilize separate gas removing assemblies.

First gas removing assembly 48 is a simple septum which is mounted through the wall of gas reservoir 12. Septum 48 is of a resilient material, e.g. rubber, which is penetrable by a hypodermic needle so that a sample of the gas in the interior of gas reservoir 12 can be withdrawn and analyzed when desired. A suitable septum would be one made of natural rubber coated with teflon. If a larger sample of gas is desired, then gas removal assembly 13 may be utilized. This assembly consists of a valved passageway communicating to the interior of gas reservoir 12. In this particular gas removal assembly, hand operated valve 26 is utilized to open and close flow of entrapped gas through gas sample line 28. Gas sample line 28 may be attached to a sample loop of a gas chromatograph apparatus wherein a direct reading of the quantity and quality of gas components may be analyzed.

Vacuum gauge 29 can be mounted between capillary 20 and valve 22 for indicating reservoir pressure. Such a gauge would be advantageous for the wearer in that he may be able to monitor the interior reservoir gas pressure and thus determine if the required pressure differential exists at any one particular time.

To aid in the carrying of the apparatus of this invention, gas reservoir 12 has attached thereto three D-rings, left D-ring 18, center D-ring 16 and right D-ring 14. These D-rings may be utilized to attach the apparatus to the wearer's belt. Of course it is to be understood that other holding assemblies, e.g. belt chips, etc., may be utilized other than the D-rings as shown in the drawings.

Gas reservoir 12 may be of any convenient volume. The particular volume chosen will be dependent upon the time period over which the apparatus of this invention is to collect the gas sample. For the same diameter capillary, orifice, nozzle or micrometer valve opening and the same pressure differential, a large volume reservoir will give a greater sampling time than a small volume reservoir. In other words, the gas reservoir volume should be tailored to meet the sample time requirements for any given set of the above variables. Determination of gas reservoir volume can be achieved by simple trial and error once a capillary size, reservoir starting pressure and sample period has been determined. Suitable reservoir volumes are hereinbefore taught.

Figure 3:
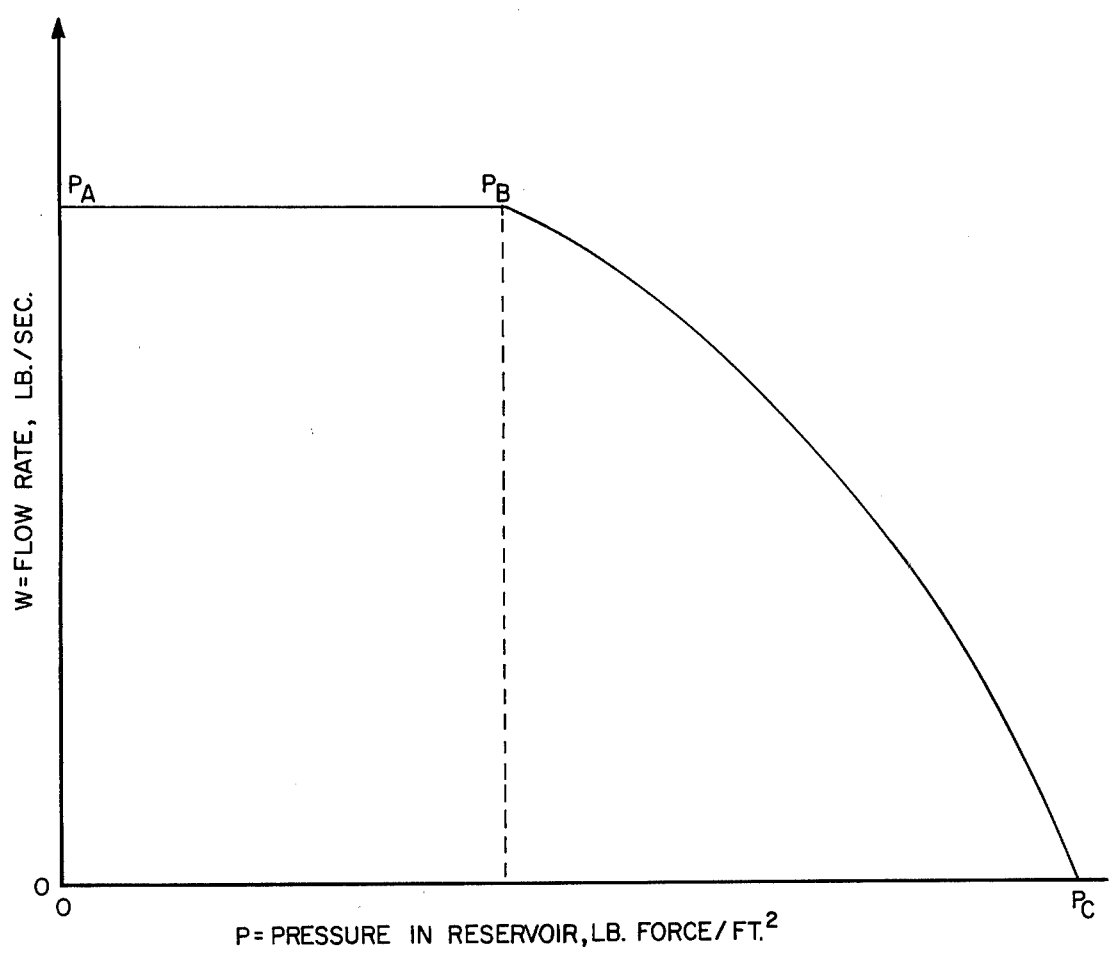
FIG. 3 is a graph of gas flow rate vs. pressure.

As mentioned previously, an object of this invention is to provide an apparatus which will collect automatically with no operator attention, a continuous time-weighted gas sample. The apparatus of this invention achieves this objective without the complex equipment and chemical adsorbents required by other present-day air sampling apparatuses. This desirable feature is achievable by the apparatus of this invention due to the fact that a gas will enter into a reservoir at a constant rate when that gas has achieved the linear velocity of sound through the aperture. Achievement of this high velocity is possible by the presence of a high pressure differential between the interior and the exterior of the reservoir. Therefore as long as the pressure differential is sufficient to maintain the linear gas velocity through the aperture at the speed of sound, the gas flow rate will be constant. Reference is had to FIG. 3 wherein this fact is graphically shown. Note that when the reservoir internal pressure is at its lowest, from $P_a$ to $P_b$, the flow rate of the gas is constant. As the reservoir interior pressure continues to increase from $P_b$ to $P_c$, $P_c$ being the ambient pressure of the gas being sampled, the required pressure differential is lost and the flow rate begins to vary towards 0. The flow rate is 0, of course, when the exterior and the interior pressure of the reservoir is the same. The time period over which the required pressure differential for constant flow rate can be maintained for any given apparatus will be dependent upon the aperture size, initial pressure differential and the reservoir volume. Determination of what minimum pressure differential will be required for any particular gas system is easily achieved by the utilization of the following formula:

$$P2/P1 = (2/[k + 1])^{k/(k - 1)}$$

wherein:

$k$ is the ratio of the specific heat of the gas at constant pressure over the specific heat of the gas at constant volume;

$P1$ is the pressure outside of the reservoir; and $P2$ is the pressure inside of the reservoir.

For further mathematical treatments to determine other variables, e.g., gas flow rates, etc., reference is had to *Chemical Engineer's Handbook*, John H. Perry, Third Edition, McGraw-Hill, pages 402–404 and to *Unit Operations of Chemical Engineering*, Warren L. McCabe, Julian C. Smith, McGraw-Hill Book Co., 1956, pages 87–88, all of which is included herein as if fully set forth.

Operation of the apparatus of this invention is the paragon of simplicity. The practitioner need only draw down the interior reservoir pressure to achieve the desired pressure differential by attaching a suction pump to hand-operated valve 26. Hand-operated valve 26 is then closed, the apparatus is attached to the worker and valve 22 is opened. Gas admittance tube 24 should be placed as close to the worker's face as possible so that the air sample gathered closely tracks the air breathed by the worker. At the end of the working period or desired sampling time, valve 22 is closed and a sample of gas is then removed from the reservoir for analysis by using either or both gas removal assemblies 13 and 48.

I claim:

1. A personal, portable apparatus worn by an operator for the continuous collection, without operator attention, of a time-weighted gas sample for subsequent analysis which comprises:

a. an enclosed gas reservoir capable of withstanding a pressure differential of about 30 inches mercury;

b. an openable and closeable gas flow means communicating with said gas reservoir for allowing gas to flow from the exterior of said reservoir to the interior of said reservoir at a constant rate when there exists a sufficient gas pressure differential between the exterior and interior of said reservoir so that the passing gas achieves a linear velocity in the throat of said gas flow means equal to the velocity of sound in said passing gas, said reservoir and said gas flow means being sized such that a sample can be obtained over a period up to about 24 hours; and c. means for attaching the apparatus to the operator.

2. The apparatus of claim 1 wherein said apparatus additionally includes a gas removing means attached to said gas reservoir for removing collected gas in said reservoir for analysis.

3. The apparatus of claim 1 wherein said gas flow means comprises a capillary tube inserted through one wall of said gas reservoir and a valve for opening and closing said capillary to said gas flow.

4. The apparatus of claim 3 wherein the inside diameter of said capillary tube is from about 0.01 mm to about 0.20 mm.

5. The apparatus of claim 2 wherein said gas removing means is a septum mounted in a wall of said reservoir, said septum being penetrable by a hypodermic needle.

6. The apparatus of claim 2 wherein said gas removing means is a valved passage extending through a wall of said reservoir.

* * * * *